(12) United States Patent
Momot et al.

(10) Patent No.: US 6,626,558 B2
(45) Date of Patent: Sep. 30, 2003

(54) APPARATUS FOR UNIFORM ILLUMINATION OF AN OBJECT

(75) Inventors: Tomasz Momot, Ossining, NY (US); Adam Jacobs, Woodcliff Lake, NJ (US)

(73) Assignee: Electro Optical Sciences Inc., Irvington, NY (US)

( * ) Notice: Subject to any disclaimer, the term of this patent is extended or adjusted under 35 U.S.C. 154(b) by 0 days.

(21) Appl. No.: 09/944,248

(22) Filed: Aug. 31, 2001

(65) Prior Publication Data

US 2002/0048170 A1 Apr. 25, 2002

(51) Int. Cl.[7] .............................................. F21Y 101/02
(52) U.S. Cl. ...................... 362/249; 362/252; 362/800; 382/128
(58) Field of Search .................................. 362/800, 249, 362/252; 382/128

(56) References Cited

U.S. PATENT DOCUMENTS

| | | | | |
|---|---|---|---|---|
| 5,580,163 A | * | 12/1996 | Johnson, II | 362/285 |
| 5,690,417 A | * | 11/1997 | Polidor et al. | 362/244 |
| 5,920,643 A | * | 7/1999 | White et al. | 382/141 |
| 6,033,087 A | * | 3/2000 | Shozo et al. | 362/244 |
| 6,070,986 A | * | 6/2000 | Yoneda | 362/33 |
| 6,491,417 B1 | * | 12/2002 | Haen et al. | 362/485 |
| 6,533,429 B2 | * | 3/2003 | Yoneda | 362/31 |

* cited by examiner

*Primary Examiner*—Laura K. Tso
(74) *Attorney, Agent, or Firm*—Rodney T. Hodgson

(57) ABSTRACT

A method, apparatus, and system for uniform illumination of an object is presented. A plurality of light sources is adjusted relative to a base in order to give a defined illumination pattern with respect to the base. Then, the light sources are rigidly affixed to the base.

17 Claims, 3 Drawing Sheets

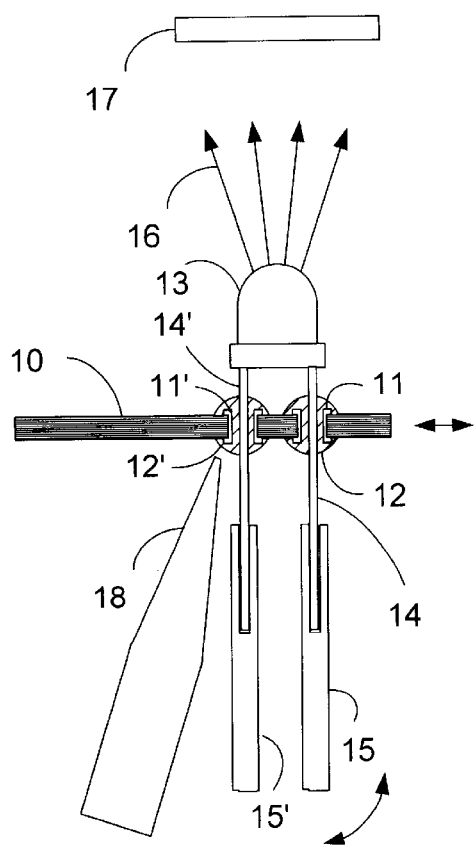
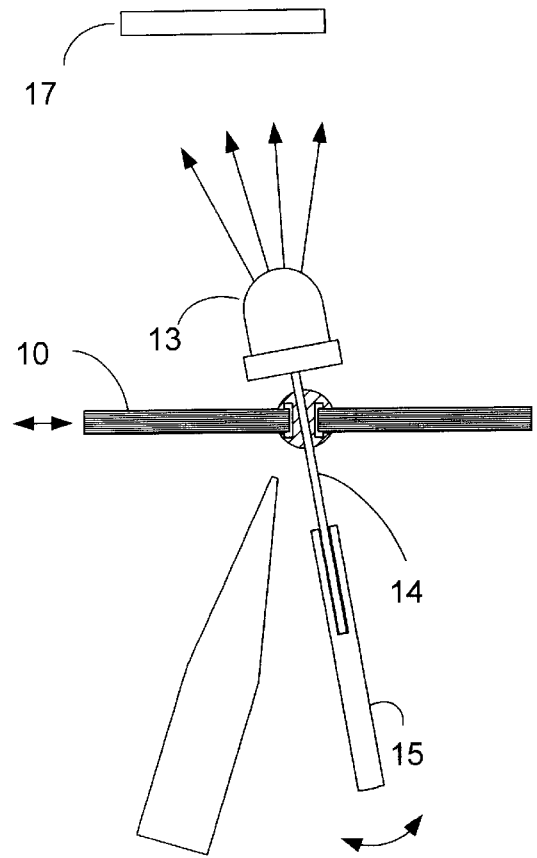
Fig. 1
Fig. 2

APPARATUS FOR UNIFORM ILLUMINATION OF AN OBJECT

RELATED APPLICATIONS

This application is a related to U.S. application Ser. No. 09/604,645, filed Jun. 27, 2000, (now U.S. Pat. No. 6,307,957 issued Oct. 23, 2001) which is a CIP of U.S. application Ser. No. 09/031,929 filed Feb. 27, 1998, (now U.S. Pat. No. 6,081,612), and U.S. application Ser. No. 09/032,450 filed Feb. 27, 1998, (now U.S. Pat. No. 6,208,749), which claim priority pursuant to 35 U.S.C. 119(e) to the following U.S. Provisional Applications: Application No. 60/039,218 and Application No. 60/039,407, both filed Feb. 28, 1997.

This application is also related to U.S. application Ser. Nos. 09/670,492, filed Sep. 26, 2000; 08/778,001 filed Dec. 31, 1996, (now U.S. Pat. No. 6,201,880, issued on Mar. 13, 2001); 09/467,344 and 09/467,345 filed on Dec. 20, 1999; 09/467345, and 09/467344; 09/722,238 filed Nov. 24, 2000, and U.S. Provisional Application No. 60/167,711 filed Nov. 27, 1999 and U.S. Provisional Application No. 60/167711 filed Nov. 22, 1999.

The above identified patents, patent applications, and references, including the references included therein, are included herein in their entirety by reference.

FIELD OF THE INVENTION

The field of illumination of an object in an imaging system, and in particular imaging of in vivo biological tissue.

BACKGROUND OF THE INVENTION

The problem of imaging biological tissue and classification of the resulting images is treated in great detail in U.S. Pat. Nos. 6,081,612 and 6,208,749, assigned to the assignee of the present invention. In order to reach the acceptable levels of accuracy in the diagnosis, for example, of melanoma, all aspects of the imaging system must be optimized. In particular, the light source used to illuminate the region of interest of the tissue must be matched particularly to the lens system and to the recording device recording the image. Prior art systems use a ring illuminator to give uniform illumination for this purpose, but the prior art system is slow and heavy, with inefficient generation of light and inefficient use of the light which is generated. In particular, prior art systems for multispectral imaging are particularly wasteful of light, as they use a rotating filter wheel and only use a small portion at a time of the spectrum of the ring light.

Prior art systems using flexible optical fiber technology to deliver light to an object require trained personnel to adjust the light source to give the required illumination. Prior art light emitting diode (LED) systems do not have sufficient power to illuminate a large area uniformly, and the LED's do not have adequate consistency from diode to diode in that the light emitted from the diode will not consistently have a well enough defined relationship between the pattern of the light produced and the body of the diode to allow the diode to be "lined up" using the physical body of the diode.

OBJECTS OF THE INVENTION

It is an object of the invention to produce an illumination system which will illuminate a body with sufficient uniformity for exacting imaging requirements. It is an object of the invention to produce an illumination system which will illuminate a body using high efficiency in the conversion of electrical energy to spectrally resolved light energy for the purpose of imaging. It is an object of the invention to produce an illumination system which will produce uniform illumination of biological tissue light over a large area. It is an object of the invention to produce an illumination system which will produce uniform illumination of biological tissue with light over a large area, where the light frequency is changed at will.

SUMMARY OF THE INVENTION

The present invention is a system, apparatus and method to produce and use a large plurality of light sources to illuminate an object with sufficient uniformity for critical imaging applications. Each of the plurality of light sources is held in adjustable relationship with a base, and the light source and the base are relatively oriented so that the illumination pattern produced by the light source bears the correct relationship with respect to the base. Once the correct relationship has been achieved, the light source is rigidly affixed to the base and the next light source is oriented and affixed.

BRIEF DESCRIPTION OF THE DRAWINGS

FIG. 1 shows a side elevation cross sectional sketch of a base and LED.

FIG. 2 shows the end elevation of the set up of FIG. 1.

DETAILED DESCRIPTION OF THE INVENTION

Figure 3:
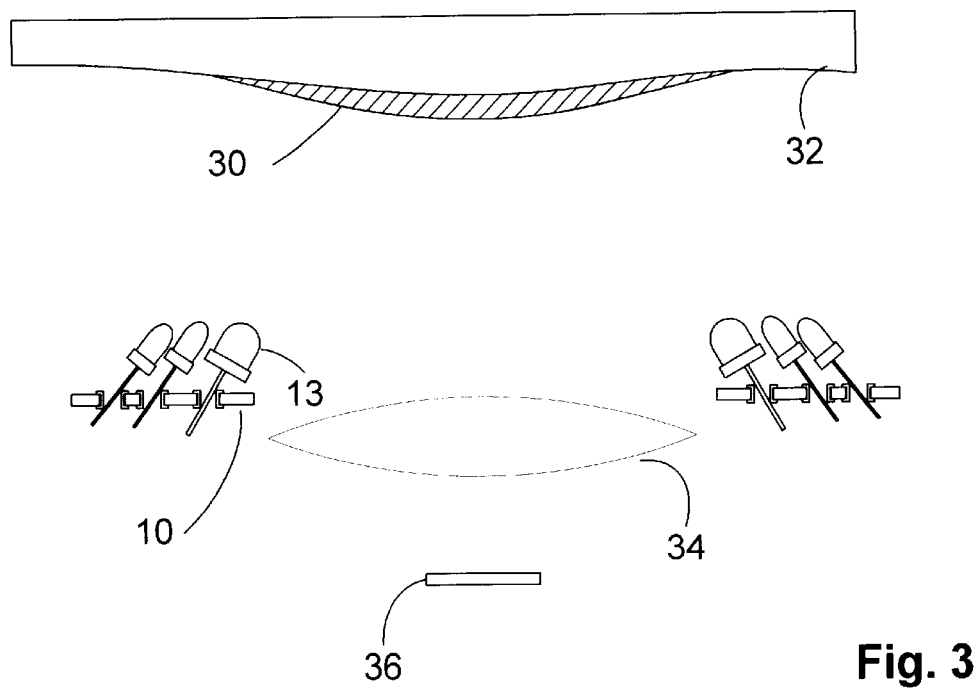
FIG. 3 shows a cross section of an illumination system using a plurality of LED's.

FIG. 1 shows a side elevation cross sectional sketch of a first embodiment of a base 10, which is shown in the sketch as a printed circuit board, having two via holes 11 and 11' filled with solder paste 12 and 12'. A light emitting diode 13 has leads 14 and 14' inserted through the solder paste 12 and 12' into holders 15 and 15' which are used both to hold the LED 13 and to supply current to the LED 13. The current is sufficient that the LED 13 produces light 16 which falls upon a detector 17 held in a known spatial relationship to the base 10. The detector may be, for example, a quadrant detector or other detector or imaging device as needed to measure the pattern of the light 16 falling on the detector. The LED 13 is manipulated by moving the holders 15 and 15' and/or base 10 relatively with respect to the detector 17 until the light pattern produced by the LED 13 and measured by detector 17 meets requirements. Then, the LED 13 is rigidly affixed to the base 10, for example in the embodiment shown in FIG. 1, by touching the solder paste 12 with a hot soldering iron 18 so that the solder paste melts and then solidifies. The vias 11 and 11' are then electrically and mechanically connected to leads in the printed circuit board 10, so that when the leads 14 and 14' are clipped, the printed circuit board will supply current to run the LED 13. While the preferred embodiment is shown as a soldering embodiment, any other methods of affixing one part to another may be used as well. In particular, laser soldering or welding, crimping, gluing or other methods of attachment of the LED leads to the base are anticipated by the inventors. The body of the LED 13 may be held by glue which rigidly attaches the LED to the base after the LED has been lined up with respect to the base. While the most preferred embodiment for a light source 13 is an LED, other light sources such as laser diodes or arc lamps are anticipated by the inventors.

FIG. 2 shows the end elevation of the set up of FIG. 1. In particular, FIG. 2 shows that the angle that the light pattern makes with respect to the base may be much larger in one direction than in another direction.

FIG. 3 shows a cross section of an illumination system using a plurality of LED's to illuminate a lesion 30 on tissue 32. Light incident on the lesion is reflected and scattered to the optical system represented by lens 34 so that the image of the lesion 30 is received on to an image receiver 36. The most preferred image receiver is a CCD array, but other image receivers as known in the art may be used as well. These include but are not limited to CMOS arrays, vidicons, or film. The plurality of LED's shown in FIG. 3 preferably include LED's which give different wavelengths of light, so that one set of diodes may be switched on to take an image using one wavelength, and then another set may be switched on to take an image using another wavelength.

A second embodiment of the invention has a plurality of the light sources aligned at the same time to form a required illumination pattern, and then the plurality of image sources is rigidly affixed to the base. The uniformity of illumination is of highest importance, so that deficiencies in uniformity of one diode may be corrected by moving another diode to make up the light in a certain portion of the illuminated area.

Figure 4:
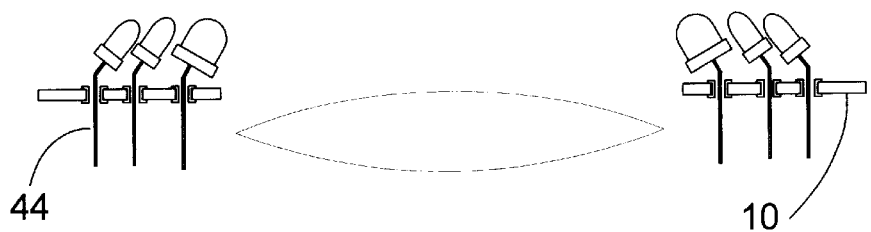
FIG. 4 shows a cross section of an illumination system using a plurality of LED's.

FIG. 4 shows an embodiment where the leads 44 of the LEDs are bent to allow adjustment of the light pattern having a large angle with respect to the plane of the base while keeping a fairly small diameter via in the printed circuit board 10.

Figure 5:
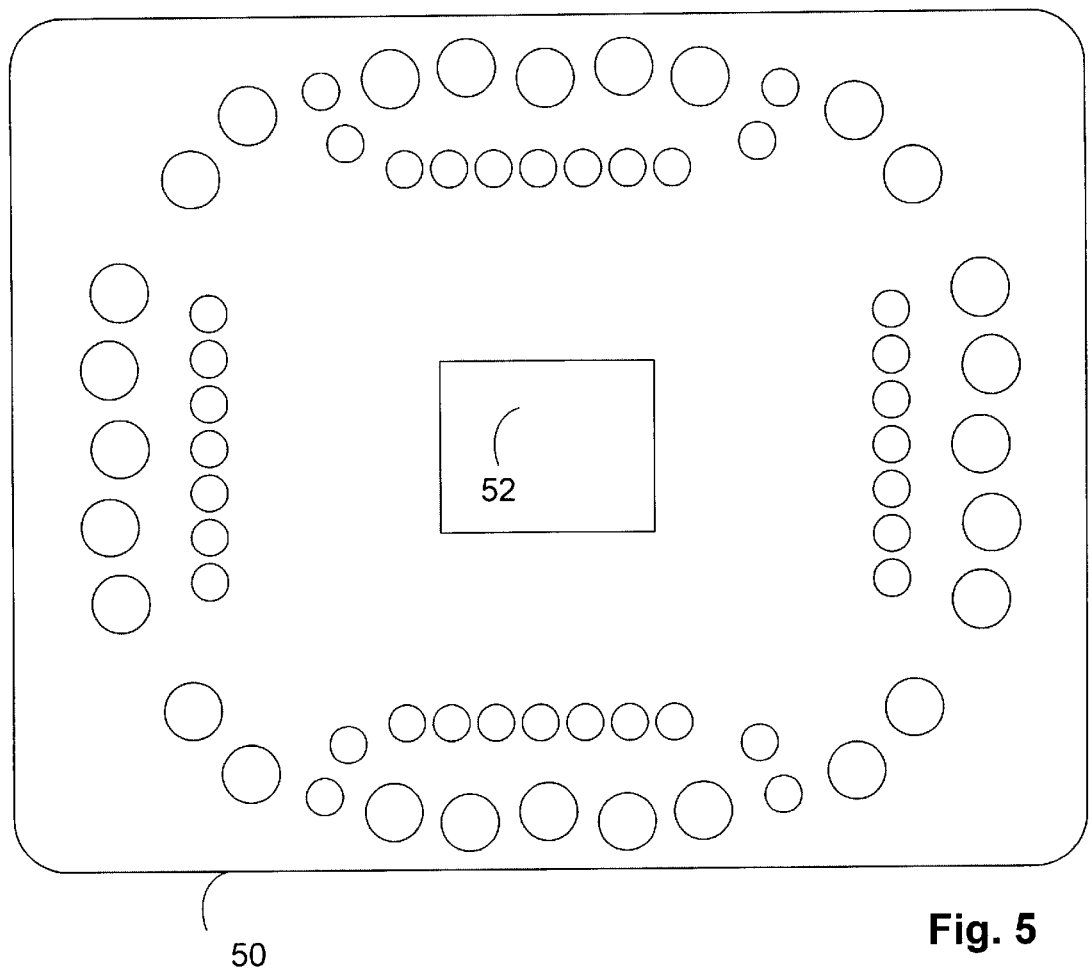
FIG. 5 shows a sketch of a plan view of a printed circuit board.

FIG. 5 shows a sketch of a plan view of a printed circuit board 50 having a hole 52 for passing light from the lesion 30 to the optical system 34 and image receiver 36. The positions of 60 LED's are noted. There are 24 LED's with nominal wavelength 430 nm (since only relatively low power LED's are currently available at such short wavelengths), and 4 each LED's with nominal wavelengths 470, 500, 550, 600, 660, 700, 770, 880, and 950 nm. Sufficient uniform illumination for imaging of a 25.6 mm by 20.48 mm lesion in 10 spectral bands in minutes with a hand held imaging device has been achieved.

Figure 6:
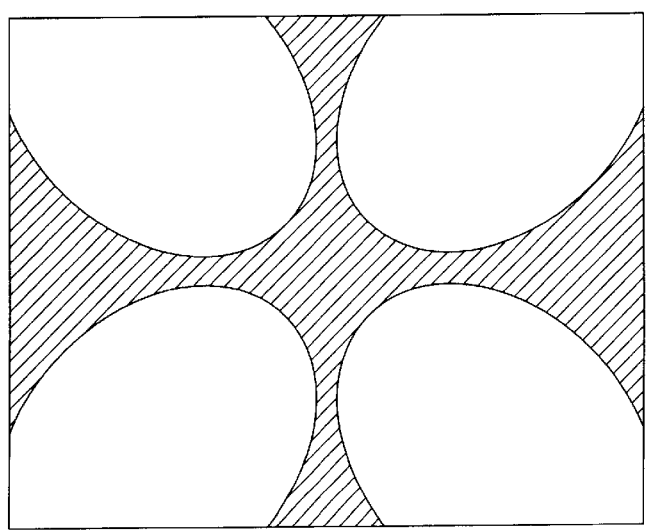
FIG. 6 shows a sketch of the illumination pattern generated by 4 of a plurality of LED's.

FIG. 6 shows the illumination pattern on a 25.6 mm by 20.48 mm field given by four LED's. The approximate lines of constant power for the half power points are shown.

Obviously, many modifications and variations of the present invention are possible in light of the above teachings. It is therefore to be understood that, within the scope of the appended claims, the invention may be practiced otherwise than as specifically described.

We claim:

1. An apparatus, comprising;
   a base;
   a large plurality of light sources fixedly attached to the base, wherein each light source has a body, and wherein at least one light source is individually adjusted with respect to the base prior to fixedly attaching the at least one light source to the base so that the at least one light source produces a defined pattern with respect to the base which is retained after fixedly attaching the at least one light source to the base.

2. The apparatus of claim 1, where at least some of the light sources are compound semiconductor devices.

3. The apparatus of claim 2, where at least some of the light sources are light emitting diodes (LED's).

4. The apparatus of claim 2, where at least some of the light sources are semiconductor laser diodes.

5. The apparatus of claim 2, where at least some of the light sources are have non-overlapping spectral ranges.

6. The apparatus of claim 5, where at least some of the light sources are in at least three spectral ranges.

7. The apparatus of claim 6, where at least some of the light sources are in at least six spectral ranges.

8. The apparatus of claim 6, where at least some of the light sources are in a spectral wavelength range up to and including the blue spectral range and at least some of the light sources are in a spectral range down to an including the near infrared spectral range.

9. The apparatus of claim 2, where the base has an aperture, and wherein the plurality of light sources surround the aperture.

10. The apparatus of claim 9, further comprising;
    a lens system attached to the base; and
    an image receiving device attached to the base, wherein the light from at least some of the plurality of lamps illuminates an object, and light reflected from and scattered from the object passes through the aperture in the base and the lens system to the image receiving device.

11. The apparatus of claim 1, where at least some of the light sources are arc lamps.

12. The apparatus of claim 1, where at least some of the light sources are tungsten halogen lamps.

13. A system, comprising;
    a base containing an aperture;
    a large plurality of light sources fixedly attached to the base surrounding the aperture, wherein each light source has a body, and wherein at least one light source has a light pattern with respect to the body of the light source which is not reproducible from light source to light source, and wherein each light source is individually adjusted with respect to the base prior to fixedly attaching the light source to the base so that each light source produces a defined pattern with respect to the base which is retained after fixedly attaching the light source to the base, and wherein at least some of the light sources are compound semiconductor devices;
    a lens system attached to the base;
    an image receiving device attached to the base, wherein the light from at least some of the plurality of lamps illuminates an object, and light reflected from and scattered from the object passes through the aperture in the base and the lens system to the image receiving device;
    a computer device attached to the base for analyzing the image received by the image receiving device; and
    communication means for communicating results of the analysis of the image with a remote communications device.

14. The system of claim 13, where the system is contained in a handheld device connected by a cable to a power source.

15. The system of claim 14, where the system communicates with a remote computer system.

16. The system of claim 13, where the system is contained in a portable cordless handheld device powered by a portable power source within the handheld device and communicating by wireless communication means.

17. The system of claim 16, where the system communicates with a remote computer system.

* * * * *